United States Patent [19]

Turkevich et al.

[11] 4,376,782

[45] Mar. 15, 1983

[54] COMPLEXES OF SQUARE PLANAR PLATINUM II COMPOUNDS AND N-METHYL GLUCAMINE

[75] Inventors: John Turkevich, Princeton, N.J.; Joseph H. Burchenal, Noroton, Conn.

[73] Assignee: Research Corporation, New York, N.Y.

[21] Appl. No.: 151,976

[22] Filed: May 21, 1980

[51] Int. Cl.³ .................. C01B 6/13; C07F 15/00; C01B 6/22
[52] U.S. Cl. ............................ 424/287; 260/429 R
[58] Field of Search .................. 260/429 R; 424/287

[56] References Cited

U.S. PATENT DOCUMENTS 4,119,653 10/1978 Tobe et al. .................. 260/429 R
4,119,654 10/1978 Tobe et al. .................. 260/429 R
4,225,529 9/1980 Hydes et al. .................. 260/429 R

OTHER PUBLICATIONS

Tobe et al., J. of Clinical Hemotogy and Oncology, vol. 7, No. 1, pp. 119 & 122, (1977), note p. 121.

Primary Examiner—Helen M. S. Sneed
Attorney, Agent, or Firm—Dennis P. Clarke

[57] ABSTRACT

Complexes or salts of square planar platinum(II) compounds and N-methyl glucamine, prepared by reacting a platinum(II) compound with N-methyl glucamine in an aqueous medium, are effective anti-tumor agents.

21 Claims, 7 Drawing Figures

COMPARATIVE ACTIVITY OF DDP, PT MALONATO AND PT MALONATO (NMG) AGAINST LEUKEMIA L1210

DOSES IN mg/kg DAYS 1, 5, 9, 13

COMPARATIVE ACTIVITY OF PT MALONATO AND PT MALONATO (NMG) AGAINST DDP RESISTENT L1210/DDP

SINGLE DOSE IN mg/kg (DAY 1)

COMPARATIVE ACTIVITY OF PT MALONATO AND PT MALONATO (NMG) AGAINST DDP RESISTANT L1210 (DDP)

DOSES IN mg/kg DAYS 1, 5, 9, 13

ACTIVITY OF COMBINATION OF PT MALONATO (NMG) AND AAFC AGAINST LEUKEMIA L1210

DOSES IN mg/kg DAYS 1, 5, 9, 13

ACTIVITY OF COMBINATION OF PT MALONATO (NMG) AND VP16 AGAINST L1210

DOSES IN mg/kg DAYS 1, 5, 9, 13

ACTIVITY OF COMBINATION OF PT MALONATO (NMG) AND AAFC OR ARA C AGAINST LEUKEMIA P388

DOSES IN mg/kg DAYS 3, 7, 11, 15

ACTIVITY OF COMBINATION OF PT MALONATO (NMG) AND MTX AGAINST LEUKEMIA P388

DOSES IN mg/kg DAYS 3, 7, 11, 15

COMPLEXES OF SQUARE PLANAR PLATINUM II COMPOUNDS AND N-METHYL GLUCAMINE

The invention described herein was made in the course of work under a grant or award from the Department of Health and Human Services.

BACKGROUND OF THE INVENTION

Square planar platinum complexes such as cis-dichlorodiammine platinum(II) [cis-$(NH_3)_2Pt(II)Cl_2$] are known to be powerful anti-tumor agents (Rosenberg et al, *J. Bacteriol*, 93, 716–721, 1967) and (Rosenberg et al, *Nature*, 222:385–386, 1969). The drug has been shown to be clinically effective against carcinoma of the testis (Einhorn et al, *Proc. Amer. Assn. Cancer Res*, 19, 29 (1978)), head and neck (Caradonna et al, *Proc. Amer. Assn. Cancer Res.*, 19, 95, (1978)) (abstract), ovary (Briscoe et al, *Proc. Amer. Assn. Res.*, 19, 72 (1978)) (abstract), bladder (Troner et al, *Proc. Amer. Assn. Cancer Res.*, 19, 161 (1978)) (abstract), and, to a lesser degree, against several other tumors (Gottlieb et al, *Cancer Chemother. Rep.*, 59:621–628 (1975)), (Hill et al, *Proc. Amer. Assn. Cancer Res.*, 13, 20 (1972))(abstract), Rossof et al, *Cancer*, 30:1451–1456, (1972)), and Talley et al, *Cancer Chemother. Rep.*, 57:465–471(1973)). In combination with bleomycin and other drugs, increased activity has been demonstrated in cancers of the head and neck (Caradonna et al, supra), esophagus (Kelsen et al, *Proc. Amer. Assn. Cancer Res.*, 19, 46 (1978))(abstract) and cervix (Slayton et al, *Proc. Amer. Soc. Clin. Onc.*, 19, 335 (1978))(abstract). This combination has also been found to be curative in a high percentage of testicular cancers (Cvitkovic et al, 19. 296 (1978))(abstract). In combination with demethyl-epipodophyllotoxin ethylidene glucoside, a high degree of activity has been shown against oat-cell carcinoma of the lung (Sierocki et al, *Proc. Amer. Soc. Clin. Onc.*, 19, 352 (1978)) (abstract). With desacetyl vinblastine amidsulfate there is increased activity with respect to epidermoid and adenocarcinomas of the lung (Gralla, R., Personal communication). In combination with cytoxan and adriamycin, activity has been reported in connection with carcinomas of the lung (Eagan et al, *Proc. Amer. Assn. Cancer Res.*, 19, 78 (1978))(abstract), bladder (Troner et al, supra) and ovary (Briscoe et al, supra).

In mouse leumemias L1210 and P388, cis-dichlorodiammine platinum(II) is markedly potentiated by 2,2'-anhydro-β-D-arabinofuranosyl-5-fluorocytosine (Burchenal et al, *Cancer Res.*, 37:4098–4100 (1977)), demethyl-epipodophyllotoxin ethylidene glucoside, 6-diazo-5-oxonorleucine, methotrexate, and, to a lesser degree, by adriamycin (Burchenal et al, *Biochimie*, 60:961–965 (1978)).

Among the disadvantages associated with di-chlorodiammine platinum(II) are the severe nausea and vomiting that it causes when administered to patients and the nephrotoxicity which severely limits the dose that can be given. In certain instances, high-tone hearing loss is also a problem. In addition, there is evidence that patients eventually develop resistance to cis-dichlorodiammine platinum(II).

In seeking solutions for these problems, various drugs, including nabilone, tetrahydrocannabinol, and metoclopramide have been used with varying degrees of success to control nausea and vomiting. Massive diuresis with intravenous infusion of mannitol has diminished the renal toxicity (Hayes et al, *Proc. Amer. Assn. Cancer Res.*, 19, 169 (1978))(abstract) but has not completely solved the problem. Currently, the upper dosage limit appears to be approximately 120 mg/$M^2$ in a single dose.

Dichloro-, malonato- and carboxyphthalato-1,2-diaminocyclohexane platinum(II) lack cross-resistance to dichlorodiammine platinum(II) and are highly effective both singly and in combinations against mouse leukemias (Burchenal et al, *Biochimie*, 60:961–965 (1978)). At the LD50 in mice, the malonato and carboxyphthalato derivatives cause much less renal toxicity than dichlorodiammine platinum(II) (Prestako et al, *Cancer Treatm. Rep.*, (in press). Several of these derivatives, however, are poorly soluble in aqueous media. Larger doses of the malonato derivative are needed than with the more soluble dichlorodiammine platinum(II). Because of the poor solubility the amount of fluid necessary to solubilize this large amount of the malonato derivative necessary for treatment of the tumor is difficult to administer safely without causing cardiovascular problems.

SUMMARY OF THE INVENTION

The solubility of and anti-tumor activity of cis-square planar platinum compounds are enhanced by forming complexes or salts thereof with N-methyl glucamine.

The complexes or salts are formed by reacting the cis-square planar platinum compound with N-methyl glucamine.

The resulting complexes or salts may be compounded in unit dosage form with a pharmaceutically acceptable carrier and administered to patients afflicted with tumors to cause a regression thereof.

DETAILED DESCRIPTION OF THE INVENTION

Figure 1:
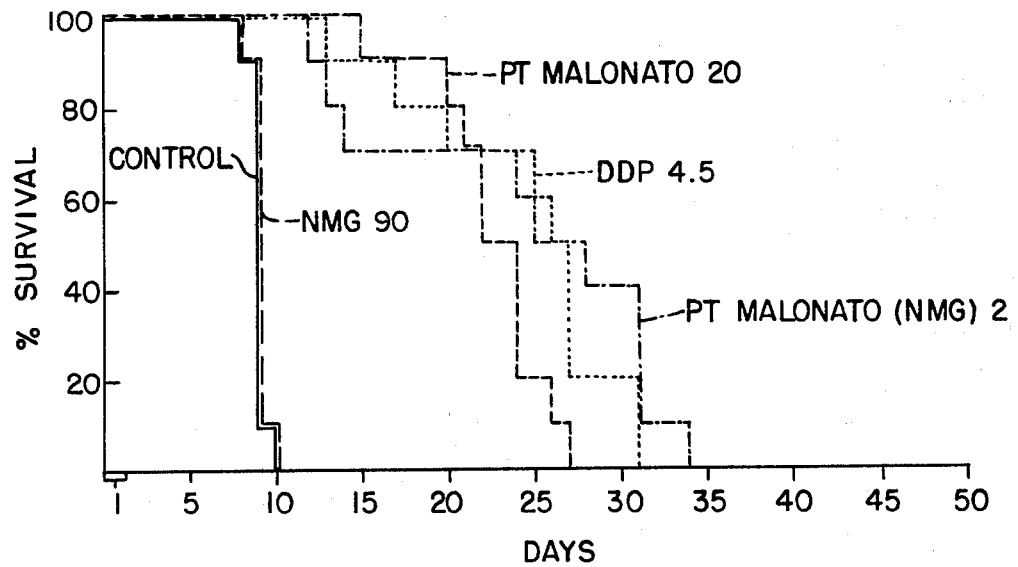

Complex or salt formation with N-methyl glucamine enhances the solubility and anti-tumor activity of a wide variety of cis-square planar platinum compounds such as e.g.

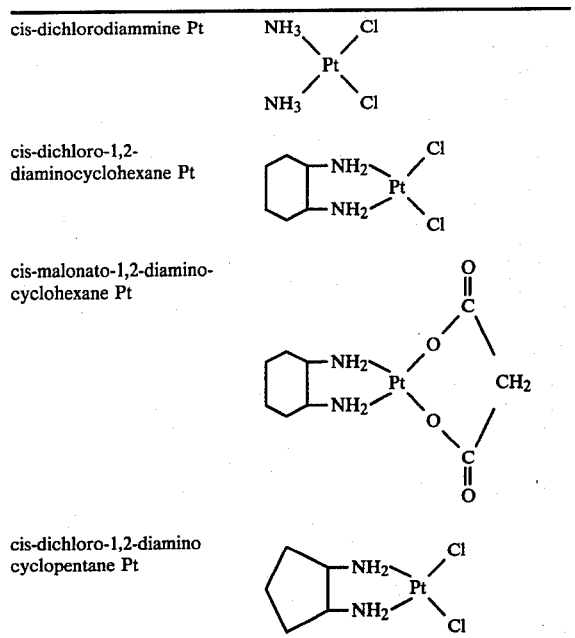

| | |
|---|---|
| cis-dichloro-1,2-diamino-cycloheptane Pt | 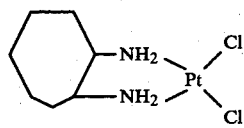 |
| cis-dichloro-ethylene-diamine Pt | 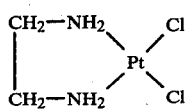 |
| cis-dichloro-bis-(isopropylamine)Pt | 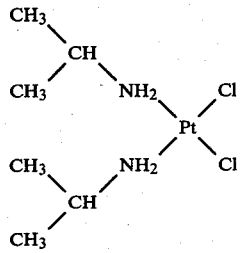 |

The complexes or salts are formed by reacting two moles of N-methyl glucamine with each mole of platinum compound, preferably in an aqueous medium.

Any square platinum compound capable of forming cis-(PtII) complexes useful as anti-cancer chemotherapeutic agents may be employed according to the present invention. Preferred platinum compounds include the haloplatinates and those exemplified hereinabove.

The exact chemical structure of the complexes or salts of the present invention is presently unknown. It is theorized, however, that since two moles of N-methyl glucamine combine with one mole of the platinum compound, the N-methyl glucamine either replaces two of the ligands of the platinum compound or are incorporated at right angles to the plane of the other atoms.

The complexes or salts of the present invention were prepared and tested according to the following procedures:

The techniques for evaluating the chemotherapeutic activity of a drug by its ability to prolong the survival time of mice with transplanted leukemia have been reported previously (Burchenal et al, Cancer Res., 37:4098–4100 (1977)). The experiments described hereinbelow were conducted with mouse leukemia L1210, P388, and P815 and their respective sublines resistant to ara-C, methotrexate, 5-fluorouracil, or cis-dichlorodiammine platinum (II) in C57BL/6 X DBA/2F$_1$ mice. L1210/DDP and P388/DDP are lines of leukemia L1210/0 and P388/0 that were treated with single 8 mg/kg doses of cis-dichlorodiammine platinum (II) 24 hours after inoculation of the leukemias over successive generations until no increase in survival time was seen with any tolerated dose of DDP, i.e., cis-dichlorodiammine platinum (II) (Burchenal et al, Proc. Amerc. Assn. Cancer Res., 19, 196 (1978)) (abstract). In all experiments, 1,000,000 leukemic cells suspended in 0.1 ml of 0.85% NaCl solution were inoculated ip into each animal, producing an ascitic leukemia that later progressed to the generalized disease. The mice were divided into groups of ten animals each, and treatment was initiated 24 hours to six days after the inoculation of leukemic cells and continued once every fourth day (days 1, 5, 9 and 13). Compounds were dissolved in 0.85% NaCl solution or sterile water or suspended in carboxymethyl cellulose (CMC) in either water or saline and injected ip.

Malonato diaminocyclohexane platinum (II) (hereinafter Pt-malonato) was solubilized by adding 100 mg of the compound to 25 ml sterile distilled water in which 200 mg of N-methylglucamine (NMG) had been dissolved. This suspension was then incubated in a water bath at 50° C. for four to eight hours with frequent stirring before complete solution was achieved. This stock solution was then kept at 4° C. and diluted to the appropriate concentration with water or 5% dextrose in water as the experiment required. The ratio of Pt compound to NMG was always 1:2 by weight unless otherwise specified.

For cell culture studies, a modification of the technique of Fischer was used (Fischer, Ann. N.Y. Acad. Sci., 76:673:680 (1958)); Schindler et al, Federation Proc., 17, 1617 (1958)) (abstract). The cells were incubated in McCoy's medium with 15% fetal calf serum. The initial inoculum was 40,000 to 60,000 leukemic cells/ml. For growth inhibition studies 0.1 ml of a 50-fold concentration of the drug in question was added to 5 ml of the cell-containing media. The tubes were set up in groups of four, loosely capped, and allowed to incubate in 5% $CO_2$ at 37° C. for 96 hours. Growth to approximately $10^6$ cells/ml occurred in the control tubes. The contents of each tube were agitated to resuspend the cells and counted on a Coulter counter. The percentages of inhibition of growth and the doses inhibiting 50% of the cell growth were calculated. Cell culture experiments were done with lines of mouse leukemia L1210, L1210/DDP, and L5178Y.

At two parts of NMG to one part of the malonato platinum compound by weight, NMG increased the solubility of the compound in water more than 40-fold. This solubilization by NMG also increased the toxicity and therapeutic effectiveness 10-fold with no apparent change in therapeutic index. Thus, whereas the optimal dose of the malonato platinum compound suspended in CMC in water is 20–30 mg/kg q4dx4, the optimal dose of the same compound solubilized by NMG in water is 2–3 mg/kg q4dx4 (Table I), although even much higher doses of NMG alone have no therapeutic activity (FIG. 1).

TABLE I

QUANTITATIVE COMPARISON OF ACTIVITY OF 1,2'-DIAMINO-CYCLOHEXANE MALONATO PLATINUM (Pt CMPD) AND PT COMPOUND-(NMG) AGAINST LEUKEMIA L1210

| COMPOUND | DOSE* | MST | ILS % |
|---|---|---|---|
| Control | — | 9.2 | — |
| Pt Cmpd | 45 | 21.1 | 129 |
| Pt Cmpd | 30 | 11.8 | 28.3 |
| Pt Cmpd(NMG) | 4.5 | 17.5 | 90.2 |
| Pt Cmpd(NMG) | 3.0 | 21.0 | 128.3 |
| Pt Cmpd(NMG) | 2.0 | 16.2 | 76.1 |

*Dose in mg/kg days 1, 5, and 9

When the combination was studied in vivo on a 1:1, 1:2 and 1:4 molar ratio of Pt malonato to NMG, maximal activity was noted at the 1:2 ratio and no significant further increase was found at the 1:4 ratio (see Table II).

TABLE II

QUANTITATIVE COMPARISON OF ACTIVITY OF
1,2'-DIAMINOCYCLOHEXANE MALONATO
PLATINUM (Pt CMPD)
AND PT MALONATO (NMG) WITH MOLAR RATIOS
OF PT MALONATO TO NMG OF 1:1, 1:2, AND 1:4
AGAINST LEUKEMIA L1210

| COMPOUND | DOSE* | MST | ILS % |
|---|---|---|---|
| Control | — | 11.0 | — |
| Pt Cmpd | 87.2 | 11.4 | 3.6 |
| Pt Cmpd | 43.6 | 20.5 | 86.4 |
| Pt Cmpd | 21.8 | 18.0 | 63.6 |
| Pt Cmpd | 10.9 | 15.4 | 40.0 |
| Pt Cmpd(NMG) (1:1) | 17.44 | 17.3 | 57.3 |
| Pt Cmpd(NMG) (1:1) | 8.72 | 20.9 | 90.0 |
| Pt Cmpd(NMG) (1:1) | 4.36 | 17.6 | 60.0 |
| Pt Cmpd(NMG) (1:1) | 2.18 | 14.5 | 31.8 |
| Pt Cmpd(NMG) (1:2) | 8.72 | 12.5 | 13.6 |
| Pt Cmpd(NMG) (1:2) | 4.36 | 20.4 | 85.5 |
| Pt Cmpd(NMG) (1:2) | 2.18 | 17.7 | 60.9 |
| Pt Cmpd(NMG) (1:2) | 1.09 | 18.1 | 64.5 |
| Pt Cmpd(NMG) (1:4) | 8.72 | 11.9 | 8.2 |
| Pt Cmpd(NMG) (1:4) | 4.36 | 21.1 | 91.8 |
| Pt Cmpd(NMG) (1:4) | 2.18 | 18.3 | 65.7 |
| Pt Cmpd(NMG) (1:4) | 1.09 | 16.9 | 53.3 |

*Dose in mg/kg days 1, 5, and 9

Surprisingly, however, in cell culture, at the very low concentrations necessary for activity, there was no difference between Pt-malonato dissolved in water and the Pt-malonato solubilized with NMG in water with both having an ID50 of approximately 0.2 μg/ml against L1210/0. They were also equally effective (ID50=0.2 μg/ml) against the DDP-resistant line (L1210/DDP) in tissue culture. (See Table III).

TABLE III

ACTIVITY OF
DDP, PT-MALONATO, PT-MALONATO(NMG)
IN WATER, AND PT-MALONATO(NMG) IN D5W
AGAINST DDP-SENSITIVE AND DDP-RESISTANT LINES
OF L1210

| COMPOUND | L1210/0 ID50 HG/ML | L1210/DDP ID50 HG/ML |
|---|---|---|
| DDP | 0.05 | 2.50 |
| Pt Cmpd | 0.22 | 0.25 |
| Pt Cmpd(NMG) in Water | 0.30 | 0.22 |
| Pt Cmpd(NMG) in D5W | 0.25 | 0.15 |

Figure 2:
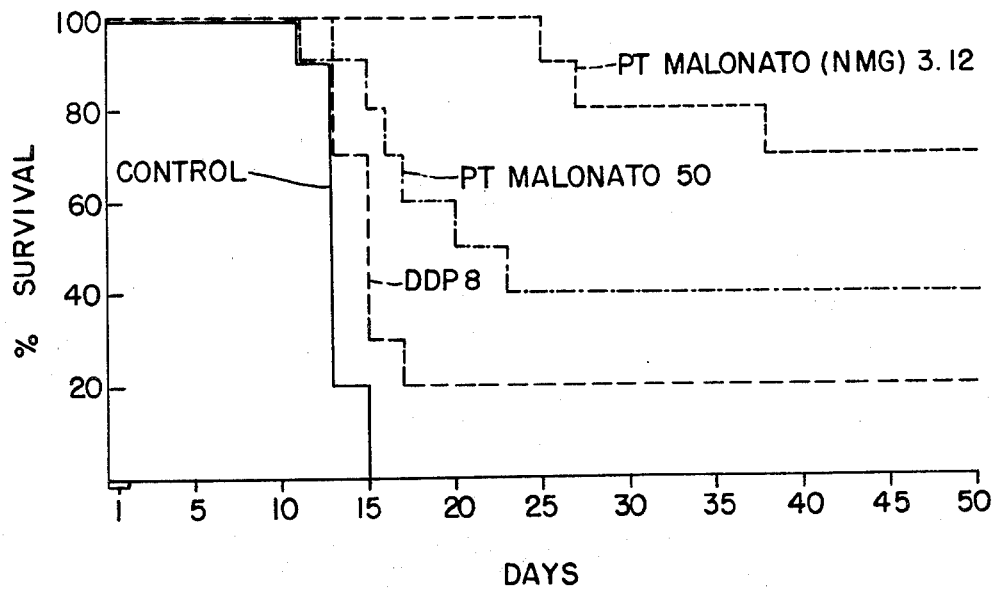
Figure 3:
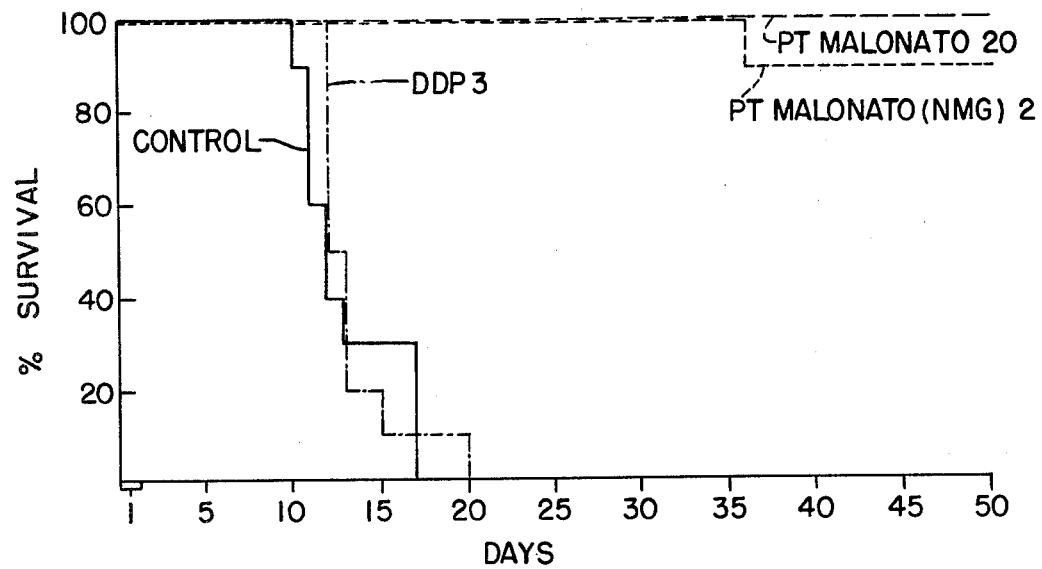
Figure 4:
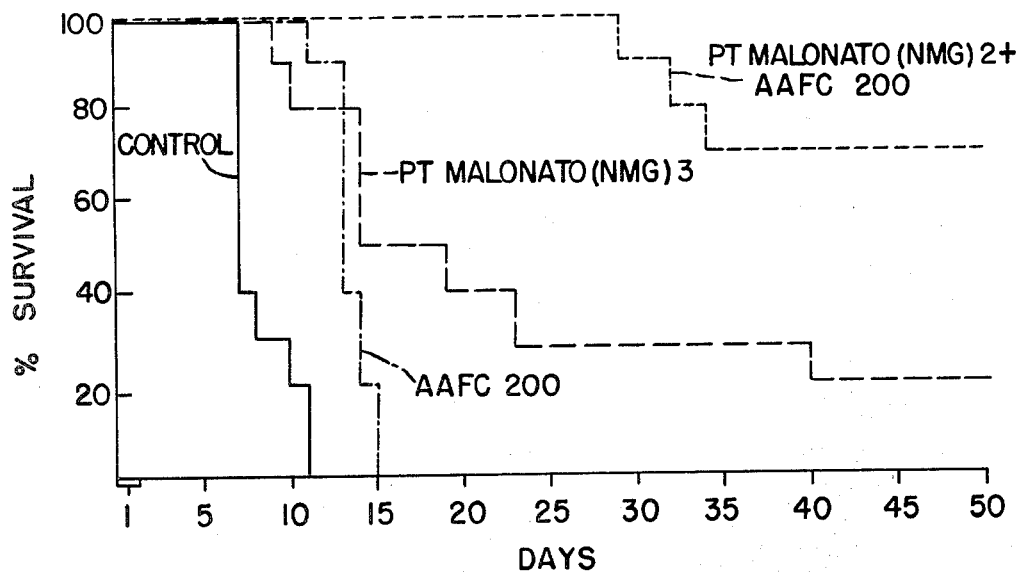
Figure 5:
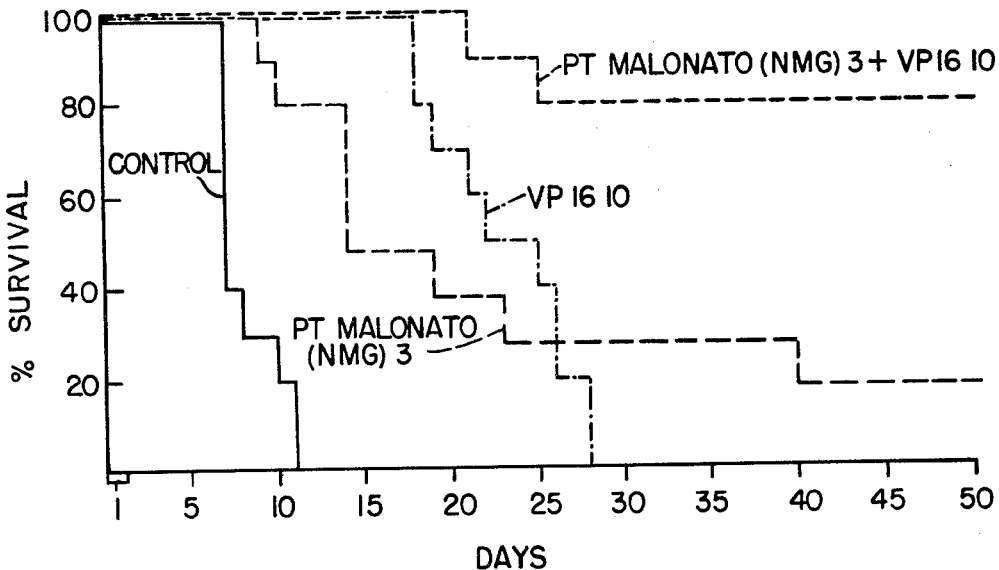
Figure 6:
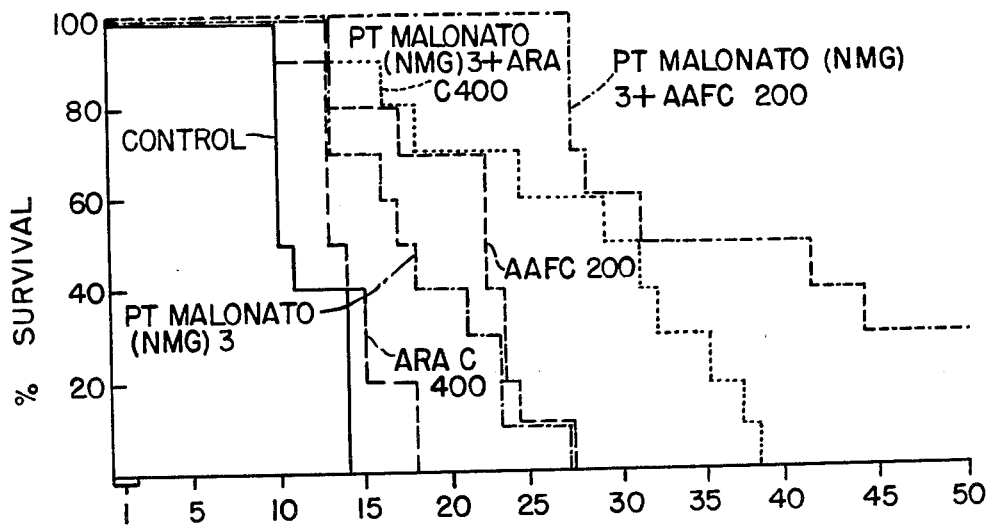
Figure 7:
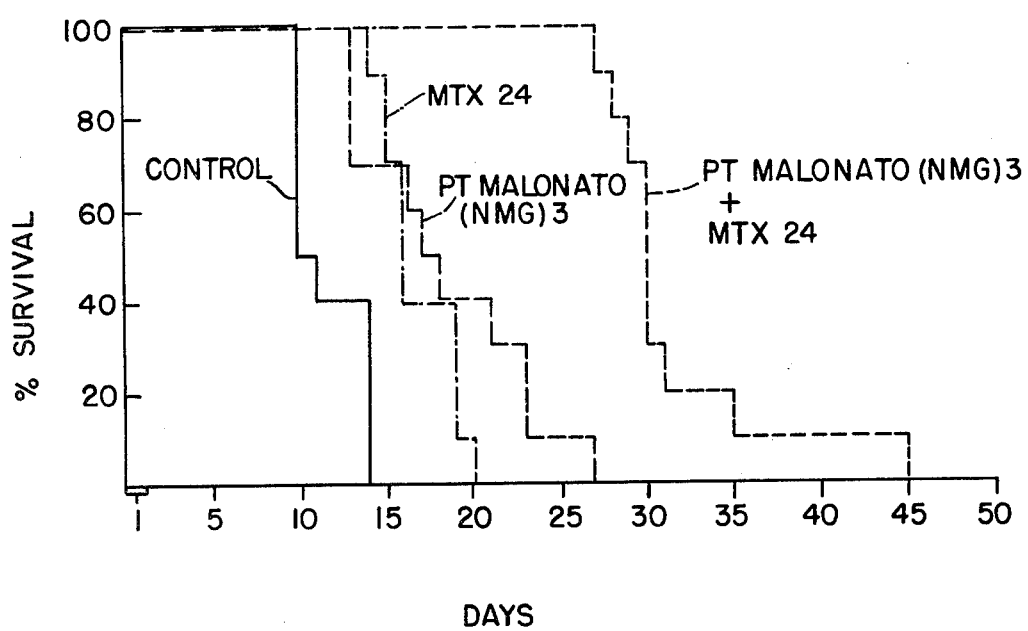

This combination of Pt-malonato solubilized in NMG (Pt-malonato-NMG) and water has been shown to be as active in vivo against the DDP-resistant lines of L1210/DDP as the parent compound in a single dose (FIG. 2) or q4dx4 schedule (FIG. 3) again at about 1/10 the dose of Pt-malonato suspended in CMC in water. Pt-malonato-NMG was additive to synergistic in combination with 2,2'-anhydro-1-β-D-arabinosyl-5-fluorocytosine (AAFC) (FIG. 4) and with demethyl-epipodophyllotoxin ethylidine glucoside (VP16) (FIG. 5) against leukemia L1210, and with AAFC, ara-C (FIG. 6), and methotrexate (MTX) (FIG. 7) against leukemia P388. It was also additive with Don and thioguanine.

Since in the patient the Pt-malonato compound dissolved in water containing NMG would probably be given to the patient in 5% dextrose in water, Pt-malonato was dissolved by the usual procedure but in 5% dextrose in water (D5W) containing NMG instead of in plain water and NMG. Surprisingly, although it was readily soluble, it showed much less toxicity and activity, having a therapeutic effect at the level usually expected from the Pt-malonato alone suspended in CMC in water, i.e., 15-50 mg/kg q4dx4. Since the concentration of glucose in D5W is roughly 50-fold the concentration of the NMG, it was considered a possibility that when NMG was first dissolved in D5W, before adding the Pt-malonato, the glucose would compete or somehow inhibit the formation of a hypothetical Pt-malonato-NMG complex, despite the fact that the drug seemed soluble. For this reason, further experiments were undertaken in which the Pt-malonato was solubilized as usual first in distilled water containing the NMG. This stock solution was then diluted down to the appropriate concentrations with distilled water for one group of mice, and D5W for the other group. When the solubilization procedure was carried out in this way, the Pt-malonato NMG was equally as potent when further diluted in D5W or in water, and no difference could be seen in either toxicity or therapeutic activity. Both were 10-fold more potent than Pt malonato suspended in CMC in water.

These studies suggest that the anti-leukemic and anti-tumor activities of the platinum derivatives are particularly susceptible to enhancement by combination with other anti-cancer agents. The formulation of the Pt compounds with NMG in water can be used to greatly increase the solubility and activity of the platinum compound without impairing their therapeutic index or their enhancement by combinations with other agents. The resultant complexes can then be diluted in D5W without changing their intrinsic properties.

I claim:

1. A cis-complex or -salt prepared by reacting a cis-square planar platinum compound with N-methyl-glucamine wherein two moles of N-methyl-glucamine are reacted with each mole of platinum compound.

2. The complex or salt of claim 1 prepared by reacting said platinum compound and N-methyl-glucamine in aqueous solution.

3. The complex or salt of claim 1 wherein said platinum compound is a haloplatinate.

4. The complex or salt of claim 1 wherein said platinum compound is cis-dichlorodiammine platinum-II.

5. The complex or salt of claim 1 wherein said platinum compound is cis-dichloro-1,2-diaminocyclohexane platinum-II.

6. The complex or salt of claim 1 wherein said platinum compound is cis-malonato-1,2-diaminocyclohexaneplatinum-II.

7. The complex or salt of claim 1 wherein said platinum compound is cis-dichloro-1,2-diaminocyclopentaneplatinum-II.

8. The complex or salt of claim 1 wherein said platinum compound is cis-dichloro-1,2-diaminocycloheptaneplatinum-II.

9. The complex or salt of claim 1 wherein said platinum compound is cis-dichloro-ethylenediamineplatinum-II.

10. The complex or salt of claim 1 wherein said platinum compound is cis-dichloro-bis (isopropylamino) platinum-II.

11. A method comprising reacting a cis-square platinum compound, and for each mole thereof two moles of N-methyl-glucamine in an aqueous medium and recovering the cis-complex or -salt of said platinum compound and N-methyl-glucamine formed therein.

12. The method of claim 11 wherein said platinum compound is a haloplatinate.

13. The method of claim 11 wherein said platinum compound is cis-dichlorodiamine platinum-II.

14. The method of claim 11 wherein said platinum compound is cis-dichloro-1,2-diaminocyclohexane platinum-II.

15. The method of claim 11 wherein said platinum compound is cis-malonato-1,2-diaminocyclohexane-platinum-II.

16. The method of claim 11 wherein said platinum compound is cis-dichloro-1,2-diaminocyclopentane-platinum-II.

17. The method of claim 11 wherein said platinum compound is cis-dichloro-1,2-diaminocycloheptane-platinum-II.

18. The method of claim 11 wherein said platinum compound is cis-dichloro-ethylene-diamine-platinum-II.

19. The method of claim 11 wherein said platinum compound is cis-dichloro-bis(isopropylamine) platinum-II.

20. A pharmaceutical composition in unit-dosage form for the treatment of animal malignant tumor cells sensitive to a complex or salt of claim 1 consisting essentially of an effective amount of said complex or salt sufficient to cause regression of said animal tumor cells and a pharmaceutically acceptable carrier therefor.

21. A method of treating animal malignant tumor cells sensitive to a complex or salt of claim 1 comprising administering to an animal afflicted with said tumor cells an effective amount of said complex or salt sufficient to cause regression of the animal tumor cells.

* * * * *